US008127771B2

(12) United States Patent
Hennings (10) Patent No.: US 8,127,771 B2
(45) Date of Patent: Mar. 6, 2012

(54) TREATMENT OF CELLULITE AND ADIPOSE TISSUE WITH MID-INFRARED RADIATION (75) Inventor: David R. Hennings, Roseville, CA (US)

(73) Assignee: CoolTouch Incorporated, Roseville, CA (US)

( * ) Notice: Subject to any disclaimer, the term of this patent is extended or adjusted under 35 U.S.C. 154(b) by 1390 days.

(21) Appl. No.: 11/675,028

(22) Filed: Feb. 14, 2007

(65) Prior Publication Data
US 2007/0142881 A1 Jun. 21, 2007

Related U.S. Application Data

(63) Continuation-in-part of application No. 11/131,577, filed on May 18, 2005, now Pat. No. 7,217,265.

(51) Int. Cl.
*A61B 19/00* (2006.01)
(52) U.S. Cl. ................. 128/898; 606/9; 607/88; 607/89
(58) Field of Classification Search ............. 606/3, 9, 606/20, 22, 23; 607/88–92, 96, 100–102; 128/898
See application file for complete search history.

(56) References Cited

U.S. PATENT DOCUMENTS

| 4,976,709 A | | 12/1990 | Sand |
| 5,102,410 A | * | 4/1992 | Dressel ........................ 606/15 |
| 5,304,169 A | | 4/1994 | Sand |
| 5,820,626 A | | 10/1998 | Baumgardner et al. |
| 5,885,274 A | | 3/1999 | Fullmer et al. |
| 5,954,710 A | | 9/1999 | Paolini et al. |
| 5,968,034 A | | 10/1999 | Fullmer et al. |
| 5,976,123 A | | 11/1999 | Baumgardner et al. |
| 6,106,516 A | * | 8/2000 | Massengill ..................... 606/15 |
| 6,206,873 B1 | * | 3/2001 | Paolini et al. ..................... 606/7 |
| 6,413,253 B1 | | 7/2002 | Koop et al. |
| 6,443,914 B1 | | 9/2002 | Costantino |
| 6,451,007 B1 | | 9/2002 | Koop et al. |
| 6,470,216 B1 | | 10/2002 | Knowlton |
| 6,605,079 B2 | * | 8/2003 | Shanks et al. ..................... 606/2 |
| 6,605,080 B1 | | 8/2003 | Altshuler |
| 6,673,096 B2 | | 1/2004 | Lach |
| 7,217,265 B2 | * | 5/2007 | Hennings et al. ................. 606/9 |
| 7,975,702 B2 | * | 7/2011 | Cho et al. ....................... 128/898 |

OTHER PUBLICATIONS

U.S. Appl. No. 10/391,221, filed Mar. 17, 2003, by Anderson et al.
U.S. Appl. No. 10/697,212, filed Oct. 30, 2003, by Hennings et al.
U.S. Appl. No. 10/351,273, filed Jan. 24, 2003, by Baumgardner et al.
U.S. Appl. No. 09/934,356, filed Aug. 21, 2001, by Koop.
U.S. Appl. No. 09/134,776, filed Aug. 1998 by Koop et al.
U.S. Appl. No. 10/738,384, filed Dec. 2003 by Hennings et al.
U.S. Appl. No. 11/131,577, filed May 2005 by Hennings et al.
U.S. Appl. No. 09/185,490, filed Jul. 2000 by Koop et al.
U.S. Appl. No. 09/135,330, filed Jul. 1998 by Koop et al.

(Continued)

*Primary Examiner* — Ahmed Farah
(74) *Attorney, Agent, or Firm* — Ray K. Shahani, Esq.; Kin H. Lai (57) ABSTRACT

A method and apparatus that will alter the fibrous strands in the fatty layers of the skin to reduce the appearance of cellulite and adipose tissue. Electromagnetic energy is used to selectively shrink or alternatively photoacoustically ablate the collagen in the constricting bands of connective tissue that causes the dimpled appearance of cellulite and adipose tissue while avoiding damage to the surrounding fatty cells.

30 Claims, 8 Drawing Sheets

OTHER PUBLICATIONS

U.S. Appl. No. 10/160,579, filed May 2002 by Koop et al.
U.S. Appl. No. 10/031,154, filed Jan. 2005 by Koop et al.
U.S. Appl. No. 08/482,208, filed Jun. 1995 by Hennings et al.
U.S. Appl. No. 08/631,800, filed Apr. 1996 by Hennings et al.
U.S. Appl. No. 10/699,212, filed Oct. 2003 by Hennings et al.
U.S. Appl. No. 10/351,273, filed Jan. 2003 by Hennings et al.; and.
U.S. Appl. No. 10/335,176, filed Dec. 2002 by Baumgardner et al.
Elisa M. Chavez, "In Vitro Study of Photothermal Laser Effects on Bovine Oral Soft Tissue", ISLD 1992, 4 pages.

* cited by examiner

TREATMENT OF CELLULITE AND ADIPOSE TISSUE WITH MID-INFRARED RADIATION

RELATED APPLICATIONS

This application is a Continuation-In-Part of related pending U.S. patent application Ser. No. 11/131,577 filed May 18, 2005 entitles TREATMENT OF CELLULITE WITH MID-INFRARED RADIATION, which is incorporated herin by reference in its entirety, and claims any and all benefits to which it is entitles therefrom.

FIELD OF THE INVENTION

This invention relates to a treatment of cellulite and adipose tissue with mid-infrared radiation, and more specifically to a method and system of selectively delivering energy to and thermally altering structures of the skin that cause the dimpled appearance of cellulite and adipose tissue.

BACKGROUND OF THE INVENTION

Cellulite is a condition of the skin characterized by the presence of hard lumps of fatty material surrounded by fibrous connective tissue that gives the skin an orange peel appearance. It is caused by degeneration of subcutaneous blood vessels and results in a thinning of the dermis and pooling of body fluids. Cellulite occurs most often on the thighs, buttocks, and upper arms of Caucasian females and is often associated with obesity.

Current treatments for cellulite include mechanical massage, exercise, weight loss, diet, and topical drug treatment. None of these treatments are very effective or long lasting. There is a need for a more effective and longer lasting way to smooth the skin of people suffering from cellulite.

Prior art has focused on damaging or removing the fatty tissue to cure cellulite and remove adipose tissue. The method may not be effective due to the fact that connecting tissue, not fat, is the true cause of cellulite. Heating of the fatty cells may be beneficial to a certain degree if the cells are encouraged to metabolize fat faster. However, the appearance as a result of damaged and dead fatty cells is not attractive cosmetically unless the residue is removed in a liposuction therapy.

Other prior art teaches stimulating the generation of new collagen with a variety of optical, electromagnetic, and cosmetic means. U.S. Pat. No. 6,443,914 issued Sep. 3, 2002 to Constantino teaches the use of ultrasound to build additional fibrous tissue through the normal body repair mechanism.

U.S. Pat. No. 6,470,216 issued Oct. 22, 2002 to Knowlton teaches the use of a radio frequency generator to heat and ablate sub-dermal fat and regenerate collagen for skin tightening. RF energy is known to be highly absorbed in fatty tissue, which works in the opposite way to the present invention that avoids melting fat tissue.

U.S. Pat. No. 6,673,096 issued Jan. 6, 2004 to Lach teaches the simultaneous delivery of infrared laser radiation in the range of 650 to 1295 nm and massage devices. It is specifically stated that the objective of the invention is to heat deep layers of tissue and cause lipolysis or decomposition of fatty tissue. This range of wavelengths may heat the fatty tissue but not targeting the connective collagen as in the present invention. In addition, it is not stated that any fluence levels is required and may be trying to perform bio-stimulation with low-level radiation. The present invention clearly requires adequately high fluence levels to shrink or denature collagen and does not require bio-stimulation to be effective.

U.S. Pat. No. 6,605,080 issued Aug. 12, 2003 to Altshuler et al. teaches a method of selectively targeting fatty tissue while avoiding damage to tissue for the purpose of fat removal. The present invention proposes exactly the opposite in order to alter the collagen containing connective tissue, which is the true cause of cellulite and to disrupt the adipose tissue. Altshuler et al. teaches that the optical absorption spectra of fatty tissue is very different from the absorption spectra of surrounding tissue because of the presence of vibrational modes in the molecules of lipids that form fatty tissue. Since both fatty tissue and water based tissue such as collagen can both be found in the same parts of the skin, the difference in these two optical absorption spectra allows a way to selectively target only one of the types of tissue while reducing the heat absorbed by the other; and henceforth preserving it. Altshuler et al. teaches only the ability to heat fat while sparing tissue. Altshuler et al. does not teach that the opposite can be applied under special conditions. Moreover, Altshuler et al. does not mention cellulite in his work involved with different wavelengths.

U.S. Pat. No. 5,304,169 issued Apr. 19, 1994 to Sand and U.S. Pat. No. 4,976,709 issued Dec. 11, 1990 to Sand teach that collagen goes through several stages of alteration when heated. At temperatures lower or around 50° C., collagen is not affected. At about 60° C., collagen may contract and shrink by about 30% without denaturization or permanent damage to the structure. It has been shown that at these temperatures the shrinkage is long term and the collagen remains viable. At temperatures>65 deg C. however the collagen will denaturize and lose its elasticity and collapse. When this happens to a connective fiber the fiber may weaken, stretch, and possibly break.

U.S. Pat. No. 6,413,253 issued Jul. 2, 2002 to Koop et al., U.S. Pat. No. 6,451,007 issued Sep. 17, 2002 to Koop et al. and U.S. Pat. No. 5,885,274 issued Mar. 23, 1999 to Fullmer et al. teach a mid-IR laser directed to the surface of the skin with energy densities of 10 to 150 J/cm2 and pulse widths of 5 to 500 msec. A pulsed cryogen cooling system is used to protect the epidermis by spraying a burst of R134a cryogen onto the treatment site immediately pre or post laser treatment.

ADVANTAGES AND SUMMARY OF THE INVENTION

The present invention relies on a combination of selective absorption by collagen in fibrous strands or connective tissue and surface cooling to prevent epidermal damage. Strands that are pulling tightly on crevasses in the skin are heated to the point of denaturization, causing them to relax, expand and release the skin outward. On the other hand, strands that connect to outward bulging areas are heated merely to the non-damaging collagen shrinkage temperature of about 65° C. so they permanently contract and help smooth the skin surface.

Lasers in the wavelength region of 1.2 μm to 1.8 μm have been used for many years to shrink and damage collagen for dermatological purposes. Altshuler specifically points out that the result of utilizing a wavelength region of 1.3 μm to 1.6 μm is extremely poor in his fat removal invention because of the poor absorption in fat within the region. Therefore, lasers in the region of 1.3 μm to 1.6 μm are very suitable to be used to selectively shrink or damage collagen in the presence of fatty tissue. The present invention recognizes this fact and combines it in a novel and unique manner with the established good collagen absorption properties of that wavelength region to make a very useful invention. This particular aspect of the present invention accomplishes the opposite of Altshuler.

The selective nature of several bands of infrared electromagnetic radiation allows the collagen to be heated without damage to the surrounding fatty tissue. A combination of selective absorption by collagen in fibrous strands and surface cooling to prevent epidermal damage enables the present invention to work. Strands that are pulling tightly on crevasses in the skin are heated to the point of denaturization, causing them to relax, expand and release the skin outward. On the other hand, strands that connect to outward bulging areas are heated merely to the non-damaging collagen shrinkage temperature of about 65° C. so they permanently contract and help smooth the skin surface.

In particular the Nd:YAG laser, when operated at a wavelength of 1.32 um, is nearly perfect to selectively damage collagen in the presence of fat. Wavelengths longer than 1.6 um will not be able to penetrate deep enough through the epidermal tissue to reach the target depth and wavelengths shorter than 1.3 um do not have enough water absorption to effectively heat the collagen strands. However, when this invention is used in a percutaneous manner utilizing a fiber optic probe, wavelengths such as 2.0 um would be very effective.

The present invention provides a system and method to shrink some of the cellulite connective strands while weakening and stretching others. Strands in the valleys of the cellulite dimples are stretched and weakened while strands near the upper hill, top or surface of the dimple are shrunk to pull the top of the dimple inward. Precise control of the heating temperature is critical to accomplish this simultaneously. Radiation fluence must be high (>1 J/cm2) enough to cause permanent shrinkage or denaturization of the collagen in the connective tissue. Low-level fluence (<1 J/cm2) will not work to break connective tissue bonds, but they may stimulate fatty tissue reduction.

The method of the present invention requires a temperature feedback device connected to the energy source. The valleys of the cellulite will be treated at a higher temperature (>70 deg C.) to break the strands and the tops of the hills of the cellulite will be treated at a lower temperature (50 to 70 deg C.) to shrink the connective strands. Pulsed cryogen cooling is used to prevent surface damage to the epidermis and allow repeated passes over the same spot to drive the heat deep. Less cooling and fluence is used to limit penetration and reduce the target temperature. The fatty tissue may be heated enough to start to metabolize faster but the selective nature of energy at a wavelength of 1320 nm passes directly through the fat to target (i.e., be absorbed by) the fibrous strands. Also, the fat is useful to maintain a smooth and healthy appearance of the skin, in contradistinction to the teachings of the prior art.

Our new invention uses multiple bursts of laser energy and cryogen spray to target a different structure. Prior to this invention it was not known how to target and damage fibrous strands without causing extensive damage to surrounding tissue. However, by selecting an energy source that matches the transmission bands of fatty tissue and also matches the absorption bands of collagen it is now possible to accomplish this. However, the target tissue is much deeper in the dermis than taught in the prior art. Fibrous strands can be 1 to 5 mm deep into tissue where the target papillary dermis in prior art is only 0.3 to 0.5 mm deep. To permit penetration of the energy deep enough it is necessary to provide multiple bursts of energy at the same spot while simultaneously cooling the epidermis to prevent damage. In one embodiment, the cooling is done in such a way that only cools the surface and not the deep target structure. Prior art teaches that the best way to do this is to use a pulsed cryogen spray cooling method.

The use of multiple bursts of energy in the present application is novel and unique. The use of pulse stacking or repeated treatments in the same spot is not preferred in the prior art because of the risk of over treating. The first pulses heat the tissue enough that the subsequent pulses are sufficient to raise the skin temperature in an uncontrolled manner that causes burns and blisters to the surface. In this new invention we show a way to measure the temperature of the skin surface during the treatment pulse sequence and to control the energy source with a feedback loop so that the skin temperature never reaches damage threshold.

The energy required in this new invention must also be delivered in a much longer time period to be effective on the deeper structures. Prior art teaches the use of pulse duration of typically about 50 msec. To reach the deeper structures we must use about 500 to 2000 msec pulse width. This longer pulse width also enables the electronics of the temperature feedback system to accurately control the energy source.

A second mode in which the present invention can be utilized is to insert a fiber optic energy delivery probe into the skin at the location of the fibrous strands and treat them directly. The use of fiber optic delivery systems for laser energy is well known in the industry, but the use of this technique with a selectively absorbing energy source to treat cellulite and adipose tissue is not obvious. Prior attempts to try this have used energy sources that did not distinguish between the collagen and the fat and the result was extensive damage to all the surrounding tissue and a poor cosmetic result. An additional improvement to this percutaneous approach is to use a fiber optic probe that directs the energy out the front or side of the distal end. This allows the probe to be placed along side the connective strands under the skin and cut in a line with the energy pointed away from the skin surface. It is also possible to perform this procedure under ultrasound imaging to more accurately locate and cut the connective strands. The use of energy in the range of 1.3-1.6 μm or 1.9 to 2.2 μm allows the strands to be cut without affecting the surrounding fatty tissue. In this embodiment the use of the more highly absorbing 2.0 um radiation such as produced by a Thulium or Holmium doped YAG crystal may be more appropriate as the use of a percutaneous fiber optic makes it unnecessary to optically penetrate the epidermis to reach the target tissue.

The energy source to utilize this invention can preferably be a laser that emits in the region of 1.3-1.6 um or it can be a broad-spectrum source such as a filament lamp, flashlamp or other white light source that has energy output in the region of 1.3-1.6 um. The use of a device described by Fullmer in U.S. Pat. No. 5,885,274 would be ideal for this application because of the large percentage of energy from a filament lamp that is present in the infrared. However, to be more effective and to not target fatty tissue the white light source can be filtered using absorbing or dielectric filters so the peak fatty tissue absorbing bands of 900-930 nm, 1190-1220 nm, and 1700-1730 nm are not included. This is the opposite of the technique taught by Altshuler. Prior art anticipating the use of white light to treat cellulite does not filter these wavelengths out of the spectrum. The mechanism of action of prior art is to raise the temperature of the fatty tissue to 42 deg C. so that the fat cells metabolize fat reducing the appearance of cellulite and adipose tissue. The prior art techniques takes several treatments and requires time for the body to metabolize and show improvement. Our new invention works on an entirely different mechanism of action which shows immediate improvement because it is not dependant on the body to react and change its biology. Our invention targets the fibrous bands in the cellulite and adipose tissue. As we break and weaken those bands immediate improvement in the appearance of cellulite and adipose tissue will be evident.

Lasers that could be used for this invention include Nd:YAG at 1320 nm, Diode lasers at 1450 nm, ER:Glass laser at 1540 nm and fiber lasers at 1550-1600 nm.

A common treatment for cellulite and adipose tissue is massage therapy or Endermologie where the cellulite and adipose tissue is stretched and circulation stimulated in the hope that the fibrous bands are weekend and the skin surface smoothed. In this treatment a vacuum is typically applied to the skin so that it is pulled up into a series of massage rollers. The skin is folded and rolled over the cellulite and adipose tissue locations. This therapy does work but the results are minimal and temporary. This therapy is beneficial to apply after treating according to this new invention to further break and disrupt the fibrous bands that have been weekend and stretched by the mid IR energy treatment. The massage therapy should be utilized after mid IR energy treatment but before the body has a chance to reform the fibrous strands that have been damaged and made weaker by the laser or white light energy.

It is yet a further object and advantage of the present invention to provide a method for treating cellulite and adipose tissue by moving the end of the optical fiber past the end of the blunt-end cannula so that heat does not impinge on the needle tip and heat it up. The smooth and blunt end of the cannula, rather than sharpened piercing tip, prevents inadvertent puncture of skin and is safer overall to use. The apparatus includes a relatively stiff or rigid polyimide coated optical fiber, optionally cleaved flat or at an angle, providing the advantage of not requiring the use of the cannula and resistance by the fiber to breakage particularly during placement or use. By extending the firing tip of the fiber optic past the blunt distal end of the cannula, the firing tip is well beyond the cannula and there is no risk of overheating the cannula.

The coating is made of a material which absorbs the laser energy at the wavelength utilized. During use, it is an advantage to cause the distal end of the coating to burn to a char during laser delivery. The char heats to a very high temperature and acts as a hot tip ablation device, having a hat, ablative cutting surface. In an embodiment of the present invention, the method using a pulsed laser in conjunction with a coated fiber such that the rapid temperature rise at the charred fiber tip causes an acoustic explosion which ablates and disrupts tissue.

The fiber can be inserted beyond or past the end of the cannula tip so that it is no longer adjacent the tip, increasing maneuverability and improving the efficiency of the cutting tip. Additionally, by moving the distal tip of the optical fiber well past the tip of the cannula there is less chance that the metal cannula will be heated by the laser beam exiting from the emitting face of the fiber, it provides an advantage to minimize heating of the tip of the cannula which if heated may cause burns to the patient's skin as it is introduced and/or withdrawn before, during or after use.

It is also an object and advantage of the invention to use a Touhy Borst clamp on the fiber as a marker to guarantee that the fiber is well beyond the cannula tip. Using an aiming beam up to 10 times or more brighter than the conventional aiming beam, the practitioner can easily determine exactly where the fiber tip is and be able to move it well past the cannula tip before firing it to ablate the undesirable connective tissue. Further objects and advantages of the present invention will be come apparent through the following descriptions, and will be included and incorporated herein.

DETAILED DESCRIPTION OF THE EMBODIMENT

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

Figure 1:
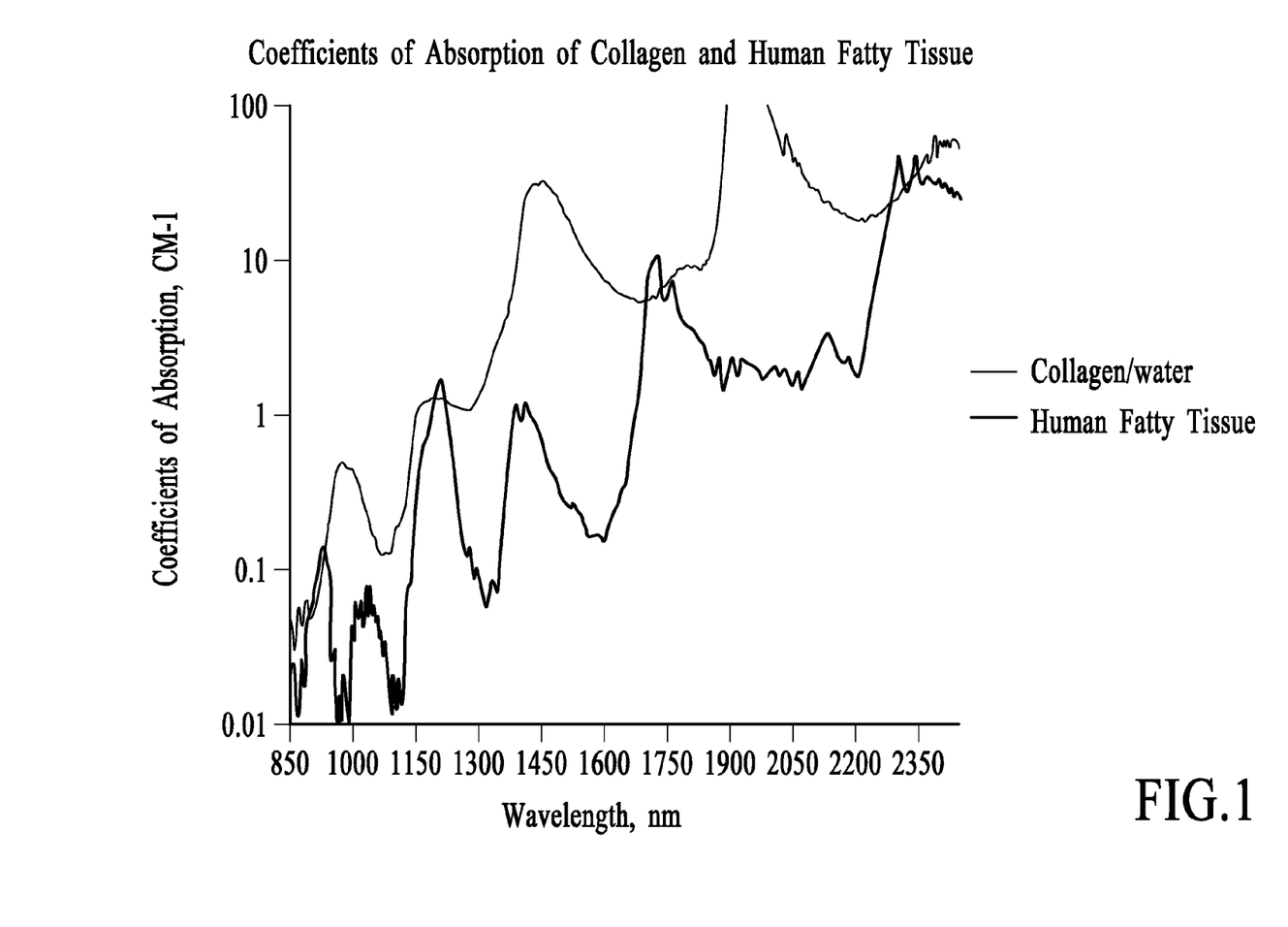
FIG. 1 is a graph illustrating the infrared absorption curves of collagen/water and human fatty tissue 124.

FIG. 1 is a graph illustrating the infrared absorption curves of collagen/water and human fatty tissue 124. The graph illustrates the coefficient of absorption (CM-1) of collagen and of human fatty tissue 124 as a function of wavelength respectively. As shown in FIG. 1, the optical absorption spectra of fatty tissue 124 is very different from that of collagen because of the presence of vibrational modes in the molecules of lipids that form fatty tissue 124. The coefficient of absorption of human fatty tissue 124 is extremely low in the wavelength region of 1.3 µm to 1.6 µm indicating poor absorption in fat within the region. The peak coefficient of absorption of fatty tissue 124 absorbing bands are 0.90µ-0.93 µm, 0.119 µm-0.122 µm, and 0.17 µm-0.173 µm. However, as also shown in FIG. 1, the coefficient of absorption of water-based collagen is relatively high in the wavelength region of 1.3 µm to 1.6 µm indicating good infrared absorption. The system 100 of present invention combines this understanding with the established high coefficient of absorption of collagen in that wavelength region. Therefore, lasers in the region of 1.3 μm to 1.6 μm are very suitable to selectively shrink or denaturize collagen containing connective tissue 122 in the presence of fatty tissue 124.

Figure 2:
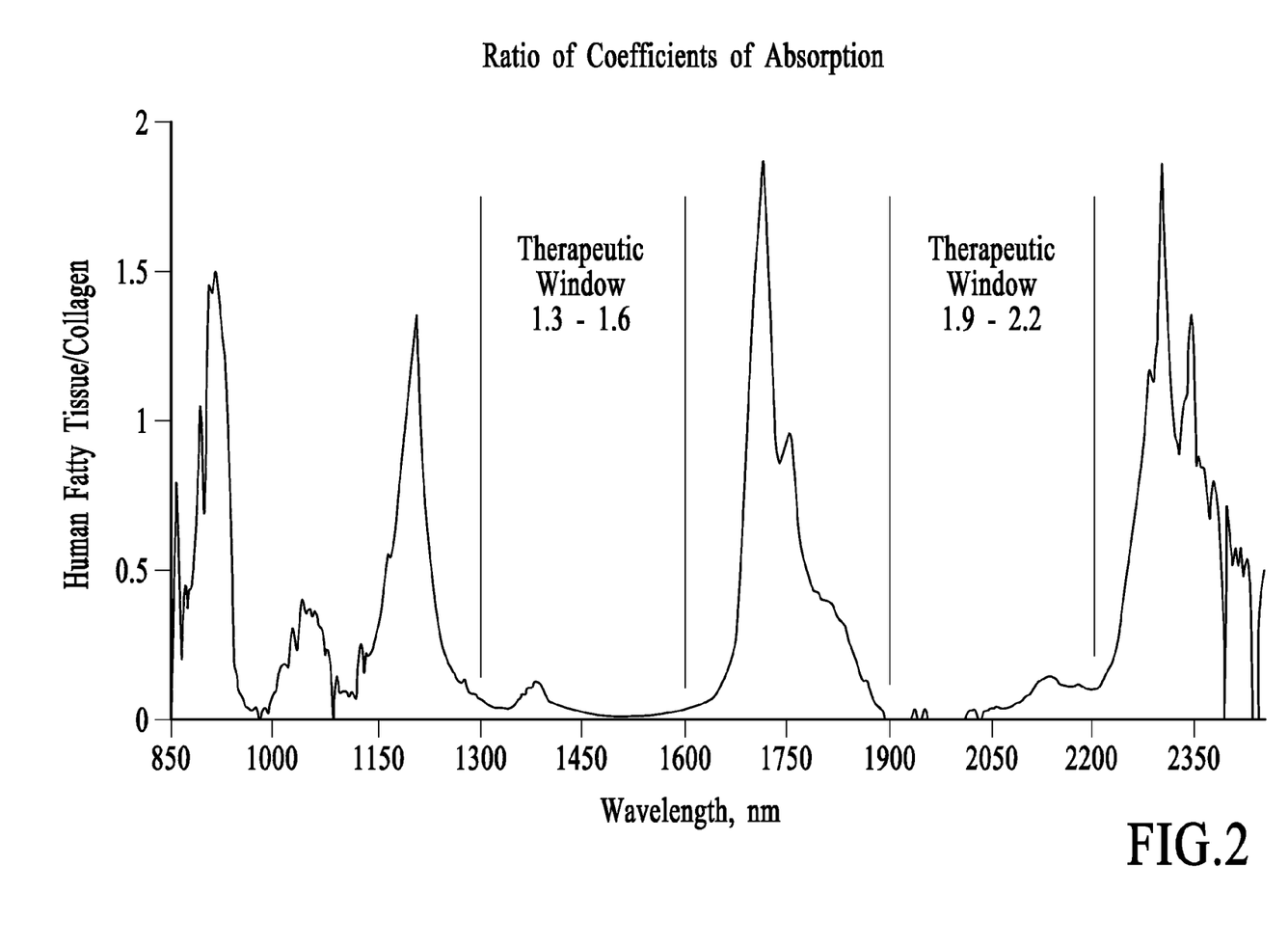
FIG. 2 is a graph illustrating the ratio of the coefficients of infrared absorption of human fatty tissue 124 and collagen as a function of wavelength.

FIG. 2 is a graph illustrating the ratio of the coefficients of infrared absorption of human fatty tissue 124 and collagen as a function of wavelength. As indicated, the higher the ratio, the larger the difference between infrared absorption of fatty tissue 124 and that of collagen; and vice versa. As shown in FIG. 2, there are windows where the ratio between fatty tissue 124 and collagen is the lowest, these are called "therapeutic windows". "Therapeutic windows" indicate the range of wavelengths where collagen containing connective tissue 122 may be effectively targeted with minimal damage to fatty tissue 124. As shown in FIG. 2, these windows occur in the wavelength range of 1.3 μm-1.6 μm and 1.9 μm-2.2 μm respectively.

Figure 3:
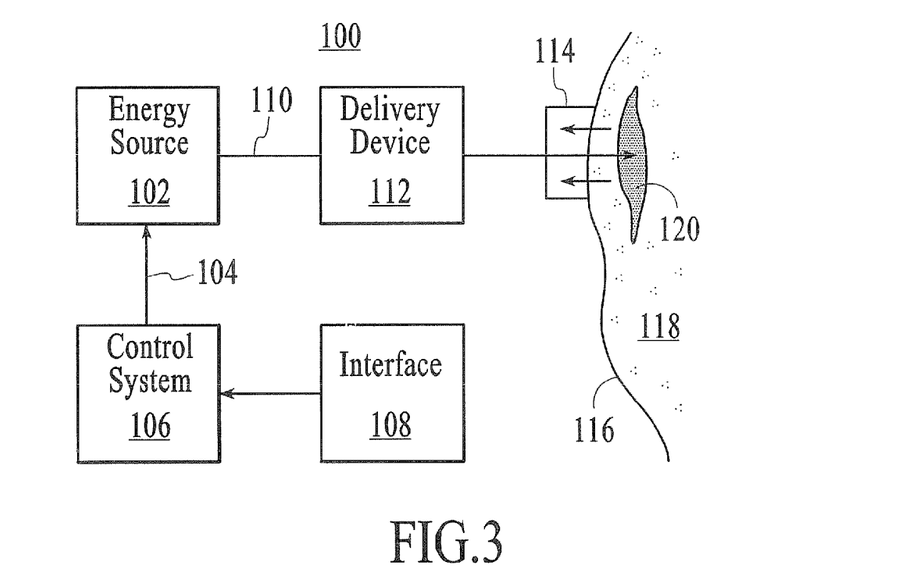
FIG. 3 is a representative schematic block diagram of one embodiment of a cellulite and adipose tissue treatment system 100 of the present invention.

FIG. 3 is a representative schematic block diagram of one embodiment of a cellulite and adipose tissue treatment system 100 of the present invention. Operation of energy source 102 to produce energy for delivery by the system 100 is controlled according to control signal 104 from control system 106. Control system 106 includes a physician interface 108 for operating the system. Said interface 108 optionally includes a footswitch (not shown) for energy delivery, display and interactive and/or menu driven operation utilizing operator input, prompts, etc. Additional energy delivery control interface means shall be known to those skilled in the art.

The energy source 102 can be a laser that emits in the region of 1.3 μm-1.6 μm or it can be a broad-spectrum source such as a filament lamp, flashlamp or other white light source that has energy output in the region of 1.3 μm-1.6 μm. The use of a device described by Fullmer in U.S. Pat. No. 5,885,274 would be ideal for the cellulite and adipose tissue treatment system 100 of present invention because of the large percentage of energy from a filament lamp that is present in the infrared. However, to be most effective and to spare fatty tissue 124, the white light source should be filtered using absorbing or dielectric filters so the peak fatty tissue 124 absorbing bands of 0.90 μm-0.93 μm, 0.19 μm-0.22 μm, and 1.7 μm-1.73 μm are not included. The prior art teaches the use of white light to treat cellulite and adipose tissue does not suggest filtering these wavelengths out of the spectrum. The mechanism of action of this prior art is to raise the temperature of the fatty tissue 124 to 42° C. so that fat cells 124 metabolize fat; resulting to a reduction of appearance of cellulite and adipose tissue.

Figure 5:
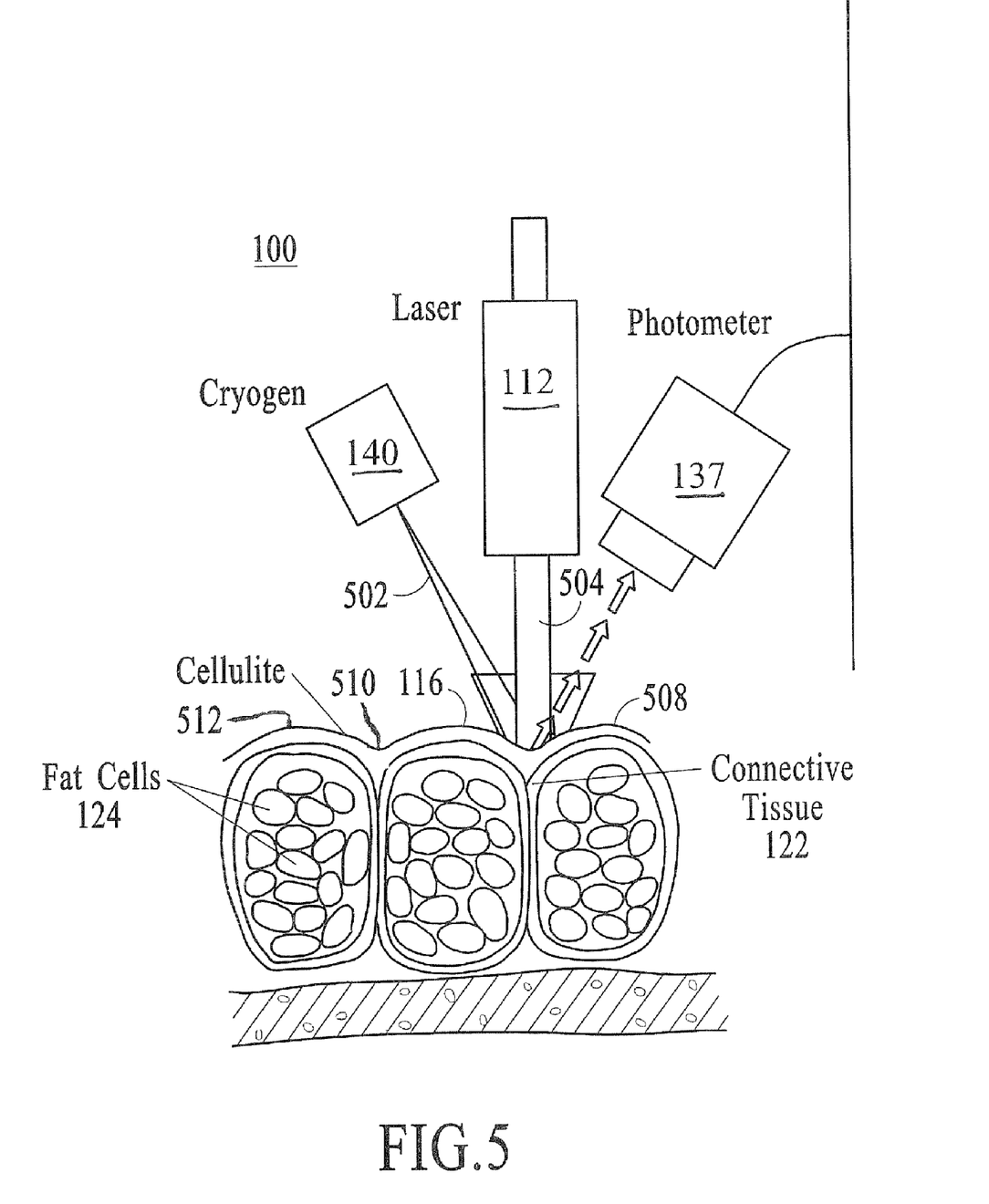
FIG. 5 is a representative detail schematic diagram of one embodiment of the cellulite and adipose tissue treatment system 100 of the present invention.
Figure 6:
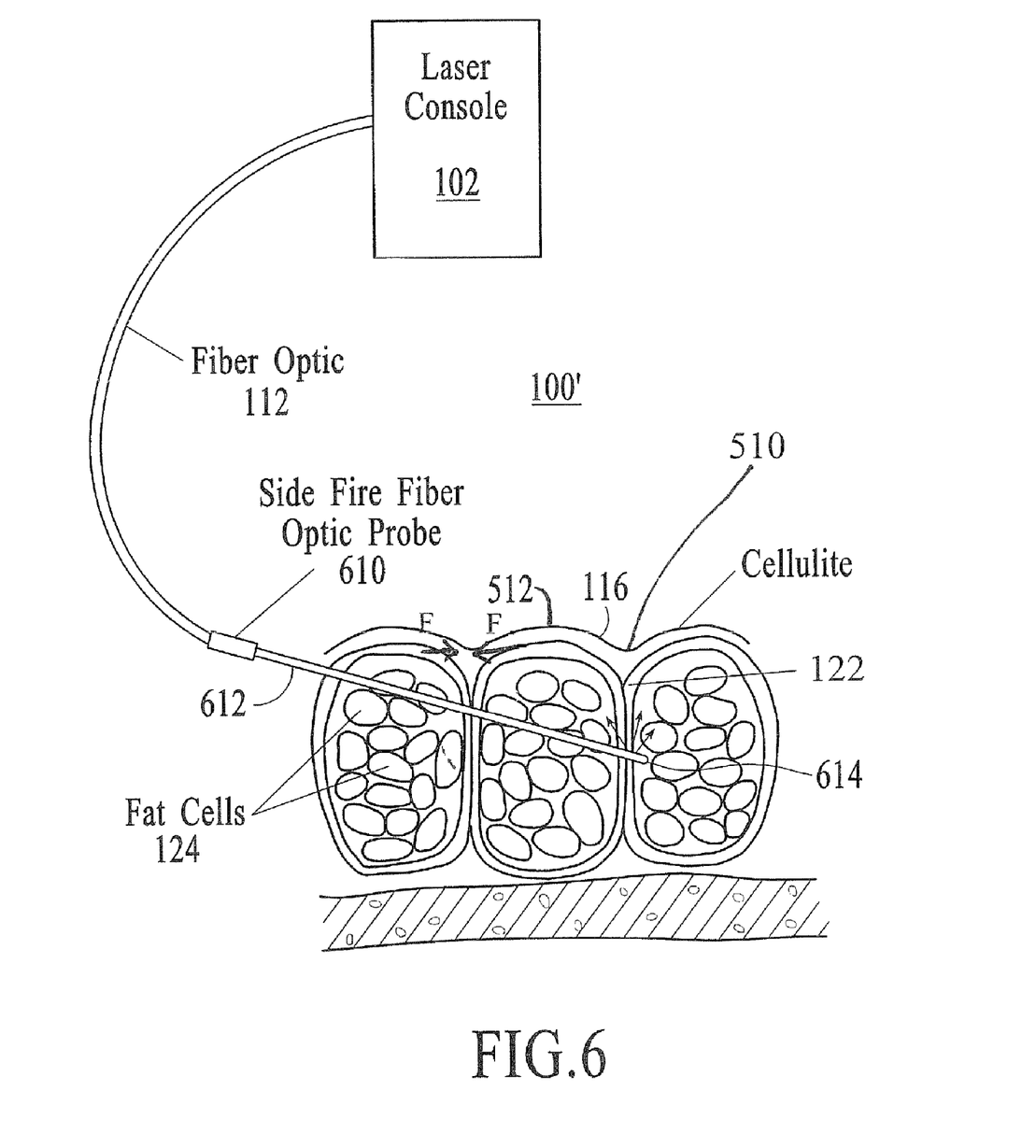
FIG. 6 is a representative detail schematic diagram of another embodiment of the cellulite and adipose tissue treatment system 100' of the present invention.

In one embodiment, energy source 102 can be a neodymium doped yttrium-aluminum-garnet (Nd:YAG) laser, energized by a flash-lamp or laser diode, at 1.32 μm, diode lasers at 1.45 μm, ER: Glass laser at 1.54 μm and fiber lasers at 1.55-1.60 μm. Energy source 102 is controlled by control system 106 which comprises the software and electronics to monitor and control the laser system, and graphical user interface 108. The beam of laser energy 110 from the energy source 102 is directed into a delivery device 112 which may be an optical fiber, a fiber bundle or articulated arm, etc. In the case of an Nd:YAG laser operated at a wavelength of 1.32 μm, it is extremely effective to selectively damage collagen containing connective tissue 122 in the presence of fat tissue 124. As best shown in FIGS. 1, 2 and 5, fatty tissue 124 may be heated enough to start to metabolize faster but the selective nature of Nd:YAG laser at 1.32 μm will allow most of the energy to transmit directly through the fatty tissue 124 to target the fibrous strands of connective tissue 122. Wavelengths longer than 1.6 μm will not be able to penetrate deep enough through the surface tissue 116 to reach the target tissue or structure 120 and wavelengths shorter than 1.3 μm do not have enough coefficients of absorption of collagen to effectively heat the collagen strands of connective tissue 122. However, as best shown in FIG. 6, wherein system 100 of the present invention is used in a percutaneous manner utilizing a fiber optic probe 610, wavelengths in the range of 2.0 μm would be very effective.

Control system 106 ensures adequate energy is delivered deep into dermis while protecting epidermis. Modern instruments to provide dynamic cooling of the surface layers of tissue or other materials are well suited to these applications. A coolant spray can be provided through a handpiece or it could be provided with another separate device. Finally, a connection to a computer and the control system 106 of the energy source 102 will allow the system 100 to utilize electronic or other thermal sensing means 700 and obtain feedback control signals for the handpiece. An optimum cooling strategy might be one that uses a post-irradiation cooling spurt that provides cooling or dissipation of the epidermal heat generated by absorption of energy in the non-isotropic skin, optionally containing various pigmentation levels. An appropriate cryogen spray 502 would be liquid nitrogen or tetrafluoroethane, $C_2H_2F_4$, an environmentally compatible, non-toxic, non-flammable freon substitute. In clinical application the distance between the aperture of the spray valve and the skin surface should be maintained at about 20 millimeters.

In one embodiment of the present invention, upon delivery of laser energy 110 onto the surface 116 and therethrough, the target tissue 120 will be raised to the optimal treatment temperature and generally not any higher, in an adequately rapid process, with the surface 116 temperature of the skin remaining at a temperature below the threshold for damage temperature. It will be understood that the threshold for damage temperature is the temperature below which the skin or other tissue can be elevated without causing temporary or permanent thermal damage, and above which the tissue may undergo either transient or long term thermally induced physiological change.

In an alternate embodiment of the present invention, surface cooling apparatus 114 such as a sapphire plate, convective or conductive cooling plate or other equivalent and efficient heat transfer mechanism may be employed to accurately control the temperature of the surface 116 of the epidermis.

Figure 4:
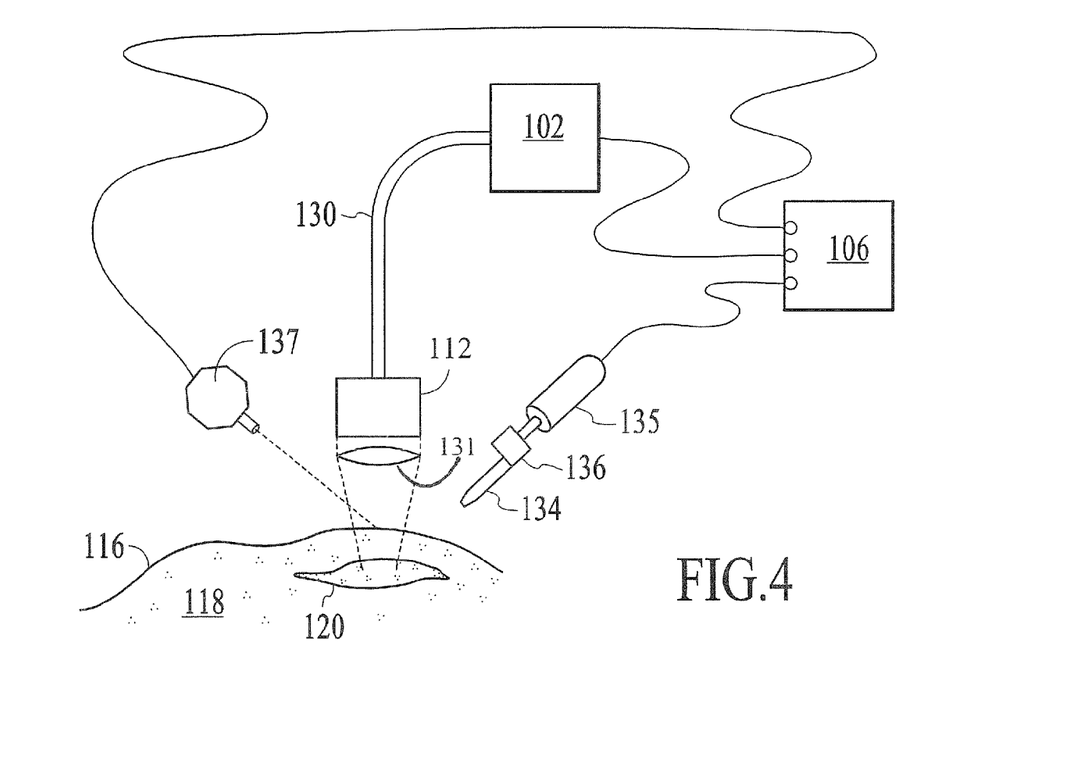
FIG. 4 is a representative schematic configuration diagram of one embodiment of the cellulite and adipose tissue treatment system 100 of the present invention.

FIG. 4 is a representative schematic configuration diagram of one embodiment of the cellulite and adipose tissue treatment system 100 of the present invention. The laser energy 110 from the energy source 102 is directed into delivery device 112 via a delivery channel 130 which may be a fiber optic, articulated arm, or an electrical cable etc. At the distal end of delivery device 112 is an energy directing means 131 for directing the pulsed energy 504 toward the surface tissue 116 and overlaying tissue 118 overlaying the target tissue or structure 120. The directing means 131 can optionally be constructed of a lens, other focusing element, lens array or other focusing configuration. A nozzle 134 is useful for directing coolant from reservoir 135 to the tissue 118, and a valve 136 for controlling the coolant interval. A visualization beam and/or temperature sensor 137 may be used to visualize target tissue 120 and/or monitor the temperature rise of the target tissue 120. Control system 106 monitors the temperature signal from sensor 137 and controls valve 136 and energy source 102. Reservoir 135 may be in the delivery device 112 or elsewhere, and contains a refrigerant 502 which may be applied to surface tissue 120 by spraying said refrigerant 502 from cooling nozzle 134 in conjunction with delivery of pulsed treatment energy 504 to the patient.

FIG. 5 is a representative detail schematic diagram of one embodiment of the cellulite and adipose tissue treatment system 100 of the present invention. The function of the delivery device 112 is to deliver mid-infrared radiation in the selective wavelength "therapeutic window" to treat sub-dermal connecting tissue 122 and also include pulsed cryogen cooling and thermal feedback.

A beam of mid infrared laser energy 504 is directed to the surface of the skin 116 with energy densities of 10 to 150 J/cm$^2$ and pulse widths of 5 to 500 msec. A pulsed cryogen cooling system 140 is used to protect the epidermis by spraying a burst of R 134a cryogen 502 onto the treatment site 508. The treatment system 100 of present invention builds on this practice. As shown in FIG. 5, multiple bursts of laser energy 504 such as Nd:YAG at 1.32 μm and cryogen spray 502 target and damage connective tissue 122 of fibrous strands without causing extensive damage to surrounding fatty tissues 124. By selecting an appropriate energy source 102 as best shown in FIGS. 1 and 2, that matches the transmission bands of fatty tissue 124 and the absorption bands of collagen, connective tissue 122 of fibrous strands can be targeted selectively without causing extensive damage to surrounding fatty tissues. Moreover, target tissue 120 of treatment system 100 of the present invention is much deeper in the dermis than that of the Koop and Fullmer patents intended. Fibrous strands 122 can be 1 mm to 5 mm deep into tissue where the target papillary dermis in prior art is only 0.3 to 0.5 mm deep. In order to address the depth issue that was not taught in prior art, it is necessary to provide multiple bursts of laser energy 504 at the same treatment site 508 while simultaneously cooling the epidermis to prevent damage by spraying cryogen 502. The cooling must be done in a way that only the skin surface 116 is cooled and not the deep target tissue 120. The task is done by using a pulsed cryogen spray cooling method that is mentioned in prior art.

As discussed, prior art does not teach multiple bursts of laser energy 504 for treatment purposes. In fact, the use of pulse stacking or repeated treatments in the same treatment site 508 is disfavored because of the risk of over treating. Theoretically, the first pulses heat the tissue enough that the subsequent pulses are sufficient to raise the skin temperature to an uncontrolled manner that could cause burns and blisters to the skin surface 116.

As shown in FIG. 5, the treatment system 100 of present invention has a temperature sensor 700 set up in a way that measures the temperature of the skin surface 116 during the treatment pulse sequence and to control the energy source 102 with a feedback loop so that the skin temperature 506 never reaches damage threshold.

Moreover, the laser energy 504 required in the treatment system 100 of present invention must also be delivered in a much longer time period than 50 msec. In the present invention, order to reach the deeper structures effectively as required by treatment system 100 of the present invention, the pulse duration should be in the range of about 500 msec to 2000 msec pulse width. The longer pulse width also enables the electronics of the temperature feedback system 700 to accurately control the energy source 102.

Collagen goes through several stages of alteration when heated. At temperatures lower or around 50° C., collagen is not affected. At about 60° C., collagen may contract and shrink by about 30% without denaturization or permanent damage to the structure. It has been shown that at these temperatures the shrinkage is long term but the collagen remains viable. At temperatures greater than 65° C. however the collagen will denaturize and lose its elasticity and simply collapse. When this happens to a collagen containing connective fiber 122, the connective tissue 122 may weaken, stretch, and possibly break.

A principle of treatment system 100 of the present invention is to selectively shrink some of the cellulite connective tissue 122 while weakening and stretching others; all while neighboring fatty tissue 124 is avoided. As shown in FIG. 5, multiple bursts of laser energy 504, which is from appropriate energy source 102 that compares and optionally matches the transmission bands of fatty tissue 124 and the absorption bands of collagen, are directed to target tissue 120. The laser energy 504 heats up connective tissue strands 122 in the valleys 510 of the cellulite dimples to the temperature range of 70° C. plus so they are stretched and weakened. At the same time, connective tissue strands 122 comprising the hill top surface 512 of the cellulite dimples are heated to the temperature range between 50° C. and 60° C. so they are shrunk to a certain degree. As a result, there is an inward pull in the direction indicated as F generated at the top of the dimples 512, collectively the appearance of cellulite is eliminated and skin surface 116 is smoothed. Pulsed cryogen cooling 502 is used to prevent surface damage to the epidermis and allow repeated passes over the same treatment site 508 to drive the heat deep enough to targeted tissue 120. Less cooling and fluence is used to keep the energy shallow and reduce the target temperature. The fatty tissue 124 may be heated enough to start to metabolize faster but the selective nature of laser energy 504 such as Nd:YAG at 1.32 μm will allow most of the energy to transmit directly through the fat tissue 124 to target the collagen containing connective fibrous strands 122. Also, the fat tissue 124 is needed to maintain a smooth and healthy appearance of the skin. As opposed to methods and systems of the prior art, fatty tissue 124 is spared during cellulite treatment of the present invention.

Precise control of various heating temperatures in different parts of target tissue 120 is critical to accomplish the procedure simultaneously. Radiation fluence must be higher than the range of 1 J/cm$^2$ to cause permanent shrinkage or denaturization of the collagen in the selected collagen containing connective tissue 122. Low-level fluence (lower than the range of 1 J/cm$^2$) is not strong enough to break connective tissue bonds. However, it might just stimulate fatty tissue 124 reduction.

In order to accomplish the crucial temperature control, as described and shown in FIG. 4, the treatment system 100 of the present invention requires a temperature or other feedback device 137 connected to control system 106 and subsequently to the energy source 102. As described above, thermal or electronic feedback data can be used to control the temperature of the target tissue 120.

FIG. 6 is a representative detail schematic diagram of another embodiment of the cellulite and adipose tissue treatment system 100' of the present invention. As shown, the laser energy 110 from the energy source 102 is directed into delivery device 112 via a delivery channel 130 which may be a fiber optic, articulated arm, or an electrical cable etc. At the distal end of delivery device 112 is a front or side fire fiber optic probe 610 for directing the pulsed energy 504 inside the target tissue 120. The front or side fire fiber optic probe 610 includes a long cannula 612 for easy access and a forward or side-firing tip 614 for safe treatment, which may optionally comprise mechanical breaking of the fibers when in contact.

In one embodiment, a fiber optic probe 610 is inserted into the target tissue 120 at the location of the connective fibrous tissue 122. Multiple bursts of laser energy 504, which are from appropriate energy source 102 that matches the transmission bands of fatty tissue 124 and the absorption bands of collagen, are emitted and treat connective fibrous tissue 122 directly. The use of fiber optic delivery systems for laser energy is well known within the industry, but the use of this technique with a selectively absorbing energy source to treat cellulite and adipose tissue is not obvious. Prior attempts to try this have used energy sources that did not distinguish between the collagen and the fat and the result was extensive damage to all the surrounding tissue and a poor cosmetic result. An additional improvement to this percutaneous approach is to use a fiber optic probe 610 that directs the energy out the front or side of the forward or side-firing tip 614. This allows the probe 610 to be placed along side the connective strands 122 under the skin surface 116 and cut in a line with the energy 504 pointed away from the skin surface 116. It is also possible to perform this procedure under ultrasound imaging to more accurately locate and treat the connective strands 122, such as those located in the valleys 510 between the dimples of the cellulite as opposed to those located in the surface tissue 512 of the cellulite tissue. The use of energy in the range of 1.3 μm-1.6 μm or 1.9 μm to 2.2 μm allows the connective tissue 122 to be treated without affecting the surrounding fatty tissue 124. In one embodiment, the use of a more highly absorbing 2.0 μm laser energy 110 such as produced by a Thulium or Holmium doped YAG crystal may be more appropriate as the use of a percutaneous fiber optic makes it unnecessary to optically penetrate the epidermis to reach the target tissue 120.

Figure 6A:
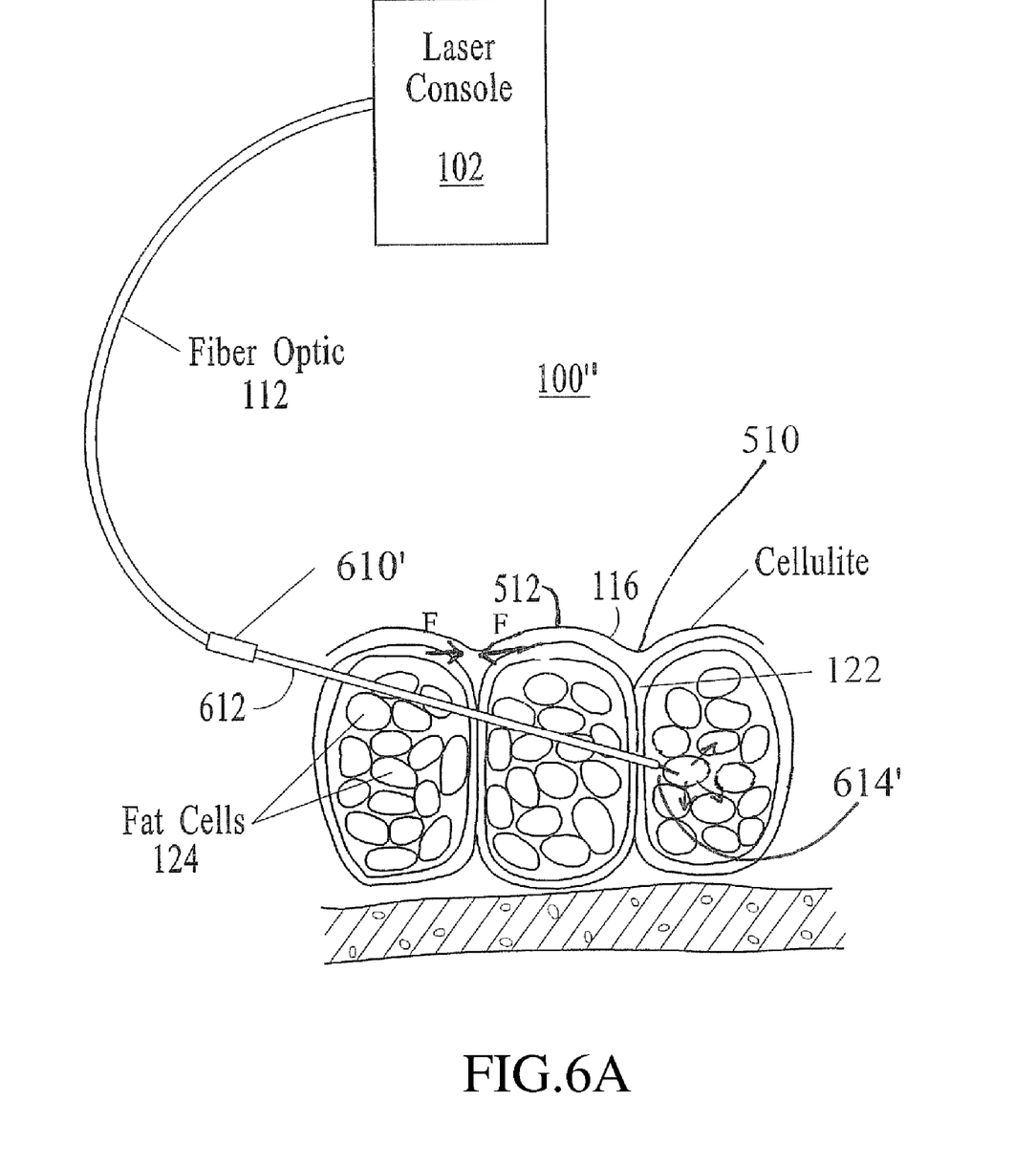
FIG. 6A is a representative detail schematic diagram of an embodiment of the cellulite and adipose tissue treatment system 100" of the present invention.

FIG. 6A is a representative detail schematic diagram of an embodiment of the cellulite and adipose tissue treatment system 100" of the present invention. As shown, the laser energy 110 from the energy source 102 is directed into delivery device 112 which may be a fiber optic, articulated arm, or an electrical cable etc. At the distal end of delivery device 112 is a front fire fiber optic probe 610' for directing the pulsed energy 504 inside the target tissue 120. The front fire fiber optic probe 610' includes a long cannula 612 for easy access and a forward firing tip 614' for safe treatment, which may optionally comprise mechanical breaking of the fibers when in contact.

Figure 7:
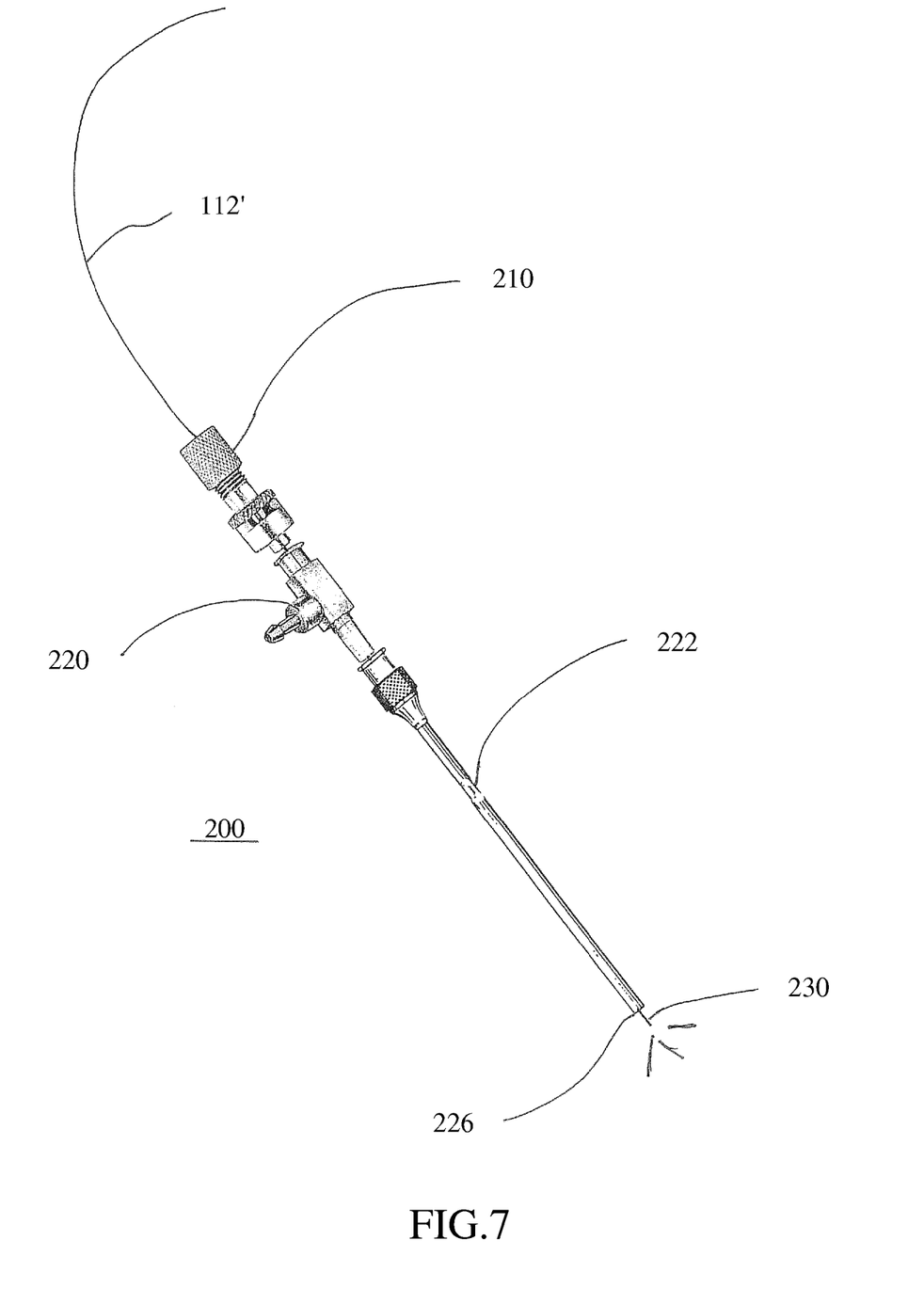
FIG. 7 is a representative detail isometric drawing of an embodiment of the cellulite and adipose tissue treatment system 200 of the present invention.
Figure 8A:
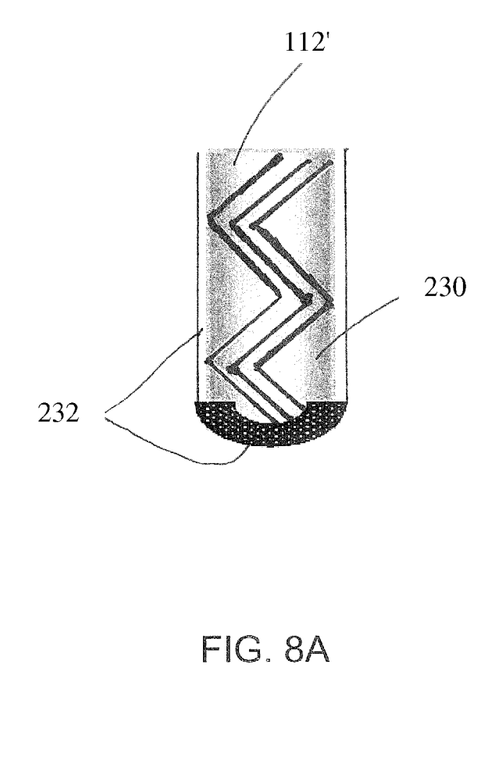
FIGS. 8A, 8B and 8C are representative section views of an embodiment of the firing tip 614' best shown in FIGS. 6A and 7.
Figure 8B:
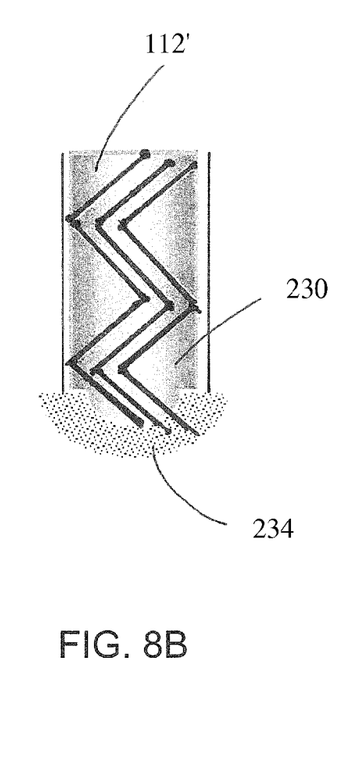
Figure 8C:
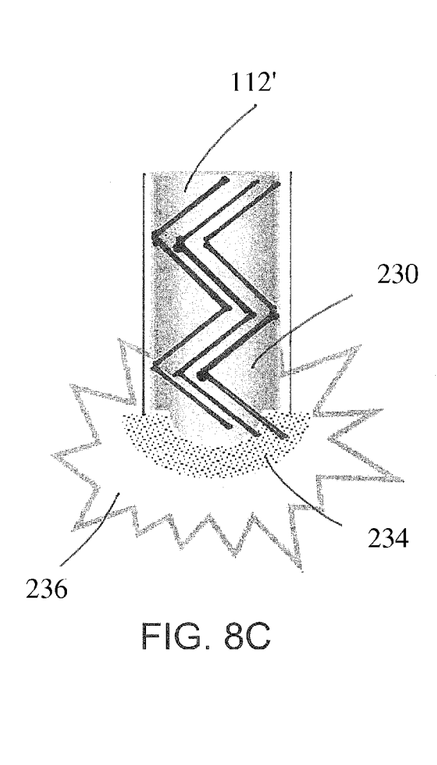

FIG. 7 is a representative detail isometric drawing of an embodiment of the cellulite and adipose tissue treatment system 200 of the present invention. FIGS. 8A, 8B and 8C are representative section views of an embodiment of the firing tip 614' best shown in FIGS. 6A and 7.

As described above with regard to FIG. 6A, an embodiment of the front fire fiber optic probe 610' comprises a coated fiber optic laser delivery device 112'. The coated fiber optic 112' is secured into a Touhy Borst or equivalent clamp 210. A side-port 220 is useful for optional aspiration of liquiified fat, blood or other tissue. As shown, the Touhy Borst clamp adapter 210 is used to fix the length of the fiber 112' so that the distal tip 230 of the fiber 112' is guaranteed to extend beyond the distal tip 226 of the cannula 222. The Touhy Borst adapter 210 essentially clamps to the fiber 112' to mark proper extension of the fiber tip 230 past the distal end 226 of the cannula 222.

As described above, the present invention is a method for treating cellulite and adipose tissue by moving the distal tip 230 of the optical fiber 112' past the blunt end 226 of the cannula 222 so that heat does not impinge on the blunt end 226 and heat it up. The smooth and blunt end 226 of the cannula 222 prevents inadvertent puncture of skin and is safer overall to use. The apparatus includes a relatively stiff or rigid polyimide coated optical fiber 112', optionally cleaved flat or at an angle, providing the advantage of not requiring the use of the cannula 222 and resistance by the fiber 112' to breakage particularly during placement or use. By extending the firing tip 230 of the fiber optic 112' past the blunt distal end 226 of the cannula 222, the firing tip 230 is well beyond the cannula 222 and there is no risk of overheating the cannula 222.

The cladding 232 of the fiber 112' is not stripped off prior to use. The fiber 112' can be cleaved through the entire coating 232. Thus, laser energy heats the coating 232 creating a carbonized tip 234. Thus, the laser energy goes mostly into heating the tip 230 and directly to target tissue. In one embodiment, the pulsed hot tip laser explodes the tissue and fat without extensive thermal effects. Fat is liquified or ablated, and the pulsed laser creates an explosively hot cutting tip 230.

The fiber coating 232 is made of a material which absorbs the laser energy at the wavelength utilized. During use, it is an advantage to cause the distal end of the coating 232 to burn to a char 234 during laser delivery. The char 234 heats to a very high temperature and acts as a hot tip ablation device, having a hat, ablative cutting surface. In an embodiment of the present invention, the method using a pulsed laser in conjunction with a coated fiber 112' such that the rapid temperature rise at the charred fiber tip 230 causes an acoustic explosion which ablates and disrupts tissue. The pulsed energy ablates a zone 236 of tissue with minimal peripheral or other unintended thermal damage. Photoacoustic ablation is similar to CW Nd:YAG sapphire crystal contact tip technology. The tip 230 requires an "initiation" to enable the carbon char 234 at the distal end 230 of the coated fiber 112' to function as a hot cutting tip. The carbon layer 234 on the tip 230 absorbs laser energy, creating an intense white hot ablation point. The system adds short pulse length pulsed energy to achieve a white hot acoustic ablation mechanism. Thus, ablation of connective tissue occurs at low energy fluences, with resultant minimal collateral damage.

The tip 230 of the coated fiber 112' can be inserted beyond or past the tip 226 of the cannula 222 so that it is no longer adjacent the cannula tip 226, increasing maneuverability and improving the efficiency of the cutting tip 230. Additionally, by moving the distal tip 230 of the optical fiber 112' well past the tip 226 of the cannula 222 there is less chance that the metal cannula 222 will be heated by the laser beam exiting from the emitting face or tip 234 of the fiber 112', it provides an advantage to minimize heating of the tip 226 of the cannula 222 which if heated may cause burns to the patient's skin as it is introduced and/or withdrawn before, during or after use.

It is also possible to use a Touhy Borst clamp 210 on the fiber 112' as a marker during other types of visualization including optical, X-ray, sonic imaging, MRI, CAT-scan or other spectral analysis visualization, to guarantee that the fiber 112' is well beyond the cannula tip 226. Using an aiming beam such as element 137 shown in FIG. 4, up to 10 times or more brighter than the conventional aiming beam, the practitioner can easily determine exactly where the fiber tip 230 is and be able to move it well past the cannula tip 226 before firing it to ablate the undesirable connective tissue.

Fat is very difficult to target using conventional selective photothermolysis. Table 1 shows the optical absorption of laser energy created by an Nd:YAG laser in fat tissue.
Optical Absorption of Nd:YAG Wavelengths:

TABLE 1

| Optical Absorption of Fat | | |
|---|---|---|
| 1064 | Fat = 0.06 | Tissue = 0.14 |
| 1320 | Fat = 0.16 | Tissue = 1.60 |

The treatment of the present invention does not depend upon optical absorption properties of fat.

The pulsed hot tip laser energy explodes tissue and fat without extensive thermal effects. Fat is liquefied, not cooked. Thus, pulsed energy at 1320 nm wavelength ablates very similar to pulsed energy at 1064 nm. Furthermore, 1320 nm also tightens the sub dermal collagen better than energy at 1064 nm.

Table 2 shows a comparison of the collateral tissue damage caused by various types of electromagnetic energy.

TABLE 2

Collateral Tissue Damage

| Device | Wavelength | Depth |
| --- | --- | --- |
| Electrocautery | #4 cut mode | 924 μm |
| Ho:YAG 2.1 μm | 4 Watts | 321 μm |
| CO2 10.6 μm | 3 Watts | 221 μm |
| Nd:YAG 1.06 μm | 3 Watts | 132 μm |
| Nd:YAG 1.32 μm | 3 Watts | 127 μm |
| Nd:YAG 1.32 μm | 4 Watts | 181 μm |

Table 3 shows the effect of pulse width, ablation width and coagulation width.

TABLE 3

Effect of Pulse Width

| Time | Ablation Width | Coagulation Width |
| --- | --- | --- |
| 120 μsec | 987 μm | 49 μm |
| 500 μsec | 593 μm | 63 μm |
| 1200 μsec | 515 μm | 81 μm |

In conclusion, shorter pulses ablate more tissue with less collateral damage to tissue. Energy at 1320 nm used for acoustic ablation shows less collateral damage than electrocautery, CO2, and Holmium lasers in a pulsed cutting mode. This is the opposite action predicted by non-contact thermal and selective photothermolysis theory. Thus, it has been shown that acoustic ablation is a new mechanism to treat tissue with low absorption.

Post-Treatment:

As mentioned above, a commonly known treatment for cellulite and adipose tissue is massage therapy or Endermologie where the cellulite and adipose tissue is stretched and circulation stimulated in the hope that the fibrous bands 122 are weakened and the skin surface 116 smoothed. During the treatment a vacuum is typically applied to the skin 116 so that it is pulled up into a series of massage rollers. The skin 116 is folded and rolled over the cellulite locations. This therapy does work but the results are minimal and usually only temporary. However, this therapy is beneficial to apply as a post-treatment. After patients are treated by the treatment system 100 of the present invention, the massage therapy can further break and disrupt the connective tissues 122 that have been weakened and stretched by the mid-IR energy treatment. The massage therapy should be utilized after mid-IR energy treatment but before the body has a chance to reform the connective fibrous strands 122 that have been damaged and made weaker by the laser or white light energy.

The present invention incorporates U.S. Pat. No. 5,820,626 issued Oct. 13, 1998 to Baumgardner and U.S. Pat. No. 5,976,123 issued Nov. 2, 1999 to Baumgardner et al. herein by reference in their entirety, without limitations, and in particular with regard to their teachings regarding surface cooling of tissue during laser treatment.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

I claim:

1. A method for treating cellulite and adipose tissue with laser energy comprising the steps of selectively targeting and treating collagen fibers in the connective structure of the tissue located essentially in the valley areas of the dimples of the cellulite and adipose tissue by photoacoustic ablation, and simultaneously selectively avoiding heating the collagen fibers in the connective structure of the tissue located essentially on the hill areas of the dimples of the cellulite and adipose tissue as well as avoiding melting of the fatty tissue of the cellulite and adipose tissue itself.

2. A method to treat cellulite and adipose tissue comprising the step of selectively targeting and treating sub-surface collagen fibers in the connective structure of the skin by photoacoustic ablation while simultaneously avoiding melting of the fatty tissue of the cellulite and adipose tissue.

3. The method of claim 2 further comprising the step of using thermal or electronic feedback to accurately control the extent of photoacoustic ablation of the target tissue.

4. The method of claim 2 further comprising the step of using thermal or electronic feedback to accurately control the heat delivered to the surrounding, non-target tissue.

5. The method of claim 2 further comprising the step of applying energy that has simultaneously low fat absorption and relatively high water absorption.

6. The method of claim 2 in which the laser energy has a wavelength in the region of between about 1.25 μm and about 1.60 μm.

7. The method of claim 2 further comprising the use of a 1320 nm Nd:YAG laser.

8. The method of claim 2 in which the laser energy has a wavelength is in the region of between about 1.3 μm and about 1.6 μm.

9. The method of claim 2 in which a flux rate of the laser energy transmitted is between about 1 J/cm$^2$ and about 150 J/cm$^2$.

10. The method of claim 2 in which the laser energy is pulsed.

11. The method of claim 10 using a pulse width of between about 1 microsecond and about 5000 microsecond.

12. The method of claim 10 using a pulse repetition rate of between about 1 and about 100 Hz.

13. The method of claim 2 in which the laser energy is delivered in a spot size of between about 0.2 cm$^2$ to about 50 cm$^2$.

14. The method of claim 2 further comprising the step of applying surface cooling to prevent undesirable epidermal damage.

15. The method of claim 14 further comprising the step of using thermal or electronic feedback to accurately control the cooling delivered to the surface skin.

16. The method of claim 14 further comprising the use of a pulsed cryogen cooling system.

17. The method of claim 14 further comprising the use of a contact surface cooling device.

18. The method of claim 2 further comprising post treatment use of massage therapy.

19. The method of claim 2 further comprising post treatment use of Endermologie.

20. The method of claim 2 further comprising the use of a percutaneous fiber probe with distal, white hot carbonized firing tip for applying laser energy directly to connective tissue.

21. The method of claim 20 further using a fiber probe with forward firing capability.

22. The method of claim 20 further comprising the step of introducing the percutaneous fiber probe through a cannula member.

23. The method of claim 22 further comprising the step of extending the firing tip of the percutaneous fiber probe beyond a distal end of the cannula prior to delivery of the laser energy.

24. The method of claim 2 further comprising the use of white light energy, optionally high in the IR, that has been filtered to remove one or more of the fatty tissue absorbing wavelength zones of between about 900 nm and about 930 nm and between about 1190 nm and about 1220 nm.

25. The method of claim 2 further comprising the step of stretching and weakening the connective tissue strands in the valleys of the cellulite and adipose tissue dimples while simultaneously shrinking the connective tissue strands in the hill top surface of the cellulite and adipose tissue dimples, thereby creating an inward pull generated at the top of the dimples collectively such that the appearance of cellulite tissue is eliminated and skin surface is smoothed.

26. The method of claim 2 in which the adipose tissue is in bags beneath the lower eyelid and the treatment reduces the appearance of the bags.

27. The method of claim 2 in which the adipose tissue is on the face and the treatment reduces the appearance of nasal labial folds.

28. The method of claim 2 in which the step of selectively targeting and treating collagen fibers in the connective structure of the tissue with heat further comprises cutting the collagen fibers in the connective structure with the laser energy.

29. A method for treatment of cellulite and adipose tissue using laser radiation utilizing a controlled system comprising (i) a laser energy source and delivery means, (ii) a cooling system and (iii) feedback detection system, the method comprising the following steps:
   (A) Delivery of laser energy sufficient to photoacoustically ablate the connective tissue strands of collagen in the valleys of the cellulite and adipose tissue dimples based upon real-time feedback thermal detection profile of the tissue strands of collagen in the valleys of the cellulite and adipose tissue dimples; and
   (B) Delivery of laser energy sufficient to shrink the connective tissue strands of collagen on the hills of the cellulite and adipose tissue dimples based upon real-time feedback thermal detection profile of the tissue strands of collagen on the hills of the cellulite and adipose tissue dimples.

30. The method of claim 29, further comprising the following step:
   (C) Applying surface cooling to the surface of the skin to prevent undesirable heating of the surface of the skin.

* * * * *